United States Patent [19]

Werbitzky et al.

[11] Patent Number: 5,723,605
[45] Date of Patent: Mar. 3, 1998

[54] BICYCLIC AMIDINES, PROCESS FOR THEIR PREPARATION, AND THEIR USE AS CATALYST

[75] Inventors: Oleg Werbitzky, Visp; Ulrich Daum, Hofstetten; Rachel Bregy, Raron, all of Switzerland

[73] Assignee: Lonza Ltd., Gampel/Valais, Switzerland

[21] Appl. No.: 339,191

[22] Filed: Nov. 10, 1994

[30] Foreign Application Priority Data

Nov. 11, 1993 [CH] Switzerland ............... 3385/93

[51] Int. Cl.$^6$ ............... C07D 243/04; C07D 239/06; C07D 235/02
[52] U.S. Cl. ............... 540/567; 544/282; 544/245; 548/302.7; 548/301.7; 540/555
[58] Field of Search ............... 540/567, 555; 544/282, 245; 548/302.7, 301.7

[56] References Cited

U.S. PATENT DOCUMENTS

| | | | |
|---|---|---|---|
| 2,957,885 | 10/1960 | Bortnick et al. | 544/282 |
| 2,984,665 | 5/1961 | Bortnick et al. | 544/282 |
| 2,993,049 | 7/1961 | Bortnick et al. | 544/282 |
| 3,761,436 | 9/1973 | Hashimoto et al. | 540/567 |
| 3,769,244 | 10/1973 | Hashimoto et al. | 521/129 |
| 4,126,685 | 11/1978 | Shaw | 548/302.7 |
| 4,507,481 | 3/1985 | Davidson et al. | 548/302.7 |
| 4,683,249 | 7/1987 | Nakatani et al. | 521/129 |
| 4,869,772 | 9/1989 | McDonnell et al. | 540/567 |

FOREIGN PATENT DOCUMENTS

| | | |
|---|---|---|
| 628948 | 10/1961 | Canada ............... 544/282 |
| 0 199 483 | 10/1986 | European Pat. Off. . |
| 1542058 | 9/1968 | France . |
| 730182 | 12/1942 | Germany . |
| 1545855 | 2/1970 | Germany . |
| 4-91121 | 3/1992 | Japan . |
| 4-96923 | 3/1992 | Japan . |
| 4-96930 | 3/1992 | Japan . |
| 4-106120 | 4/1992 | Japan . |
| 4-120127 | 4/1992 | Japan . |
| 913935 | 12/1962 | United Kingdom ............... 548/302.7 |
| 1121924 | 7/1968 | United Kingdom ............... 544/282 |
| 1182014 | 2/1970 | United Kingdom . |
| 1327464 | 8/1973 | United Kingdom ............... 544/282 |

OTHER PUBLICATIONS

Synthetica Merck, vol. II. E. Merck, Darmstadt, (1974), pp. 118,119 and 124.
W. Reppe et al., Justus Liebigs Ann. Chem., 596, (1955), p. 211.
Möhrle et al., Pharmazie, vol. 47, No. 6, (1992), pp. 403 to 409.

Primary Examiner—Rabon Sergent
Attorney, Agent, or Firm—Fisher, Christen & Sabol

[57] ABSTRACT

The process for the preparation of bicyclic amidines of the general formula:

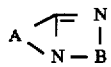

I wherein A is selected from the group consisting of —$CR^1R^2$—$CR^3R^4$—$CR^5R^6$—, —$CR^1R^2$—$CR^3R^4$—$CR^5R^6$—$CR^7R^8$— and —$CR^1R^2$—$CR^3R^4$—$CR^5R^6$—$CR^7R^8$—$CR^9R^{10}$—, wherein the substituents in A are in each case numbered starting from the nitrogen atom, and B is selected from the group consisting of —$CR^{11}R^{12}$—$CR^{13}R^{14}$—, —$CR^{11}R^{12}$—$CR^{15}R^{16}$—$CR^{13}R^{14}$— and —$CR^{11}R^{12}$—$CR^{15}R^{16}$—$CR^{17}R^{18}$—$CR^{13}R^{14}$—, and $R^1$, $R^2$ and $R^{11}$ to $R^{14}$ are, in each case independently of one another, hydrogen, $C_1$–$C_4$-alkyl, aryl, or are $C_1$–$C_4$-alkyl which is substituted with hydroxyl, amino, $C_1$–$C_4$-alkylamino or mercapto, and $R^3$ to $R^{10}$ and $R^{15}$ to $R^{18}$ are, in each case independently of one another, hydrogen, $C_1$–$C_4$-alkyl, aryl, hydroxyl, amino, $C_1$–$C_4$-alkylamino or mercapto, or are $C_1$–$C_4$-alkyl which is substituted with hydroxyl, amino, $C_1$–$C_4$-alkylamino or mercapto. The process includes heating (reacting) a lactone of the general formula:

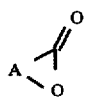

II wherein A is as defined above, to at least 150° C. together with an at least equimolar quantity of an amine of the general formula:

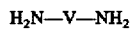

III wherein B is as defined above. The resultant reaction mixture is subjected, without isolating an intermediate, to a fractional distillation.

8 Claims, No Drawings

BICYCLIC AMIDINES, PROCESS FOR THEIR PREPARATION, AND THEIR USE AS CATALYST

BACKGROUND OF THE INVENTION

1. Field of the Invention

The invention relates to a novel process for the preparation of bicyclic amidines by reaction of lactones with primary amines. The invention also relates to novel bicyclic amidines having functional groups, especially amino, hydroxyl and/or mercapto groups, and to their use as catalysts for the preparation of polyurethanes.

2. Background Art

Bicyclic amidines are strong organic bases which, owing to their high basicity coupled with low nucleophilicity and their ready solubility in almost all solvents, have found numerous applications. Particularly well-known bicyclic amidine compounds are those commonly referred to by the abbreviations DBN and DBU, i.e., 1,5-diazabicyclo[4.3.0] non-5-ene (2,3,4,6,7,8-hexahydropyrrolo[1,2-a]pyrimidine) and 1,8-diazabicyclo[5.4.0] undec-7-ene(2,3,4,6,7,8,9,10-octahydropyrimido[1,2-a]azepine), respectively.

A review of the uses of these compounds in chemical syntheses can be found, for example, in *Synthetica Merck*, Volume II, E. Merck, Darmstadt, (1974), pp. 118–119 and 124.

A known process for preparing bicyclic amidines starts from N-(ω-aminoalkyl)lactones which, when heated with acidic catalysts, undergo cyclization with elimination of water to form the amidines (German Patent No. C 1,545, 855). The N-(ω-aminoalkyl)lactones are obtained, for example, from the corresponding cyano compounds by hydrogenation; in particular, for example, N-(γ-aminopropyl)pyrrolidone is obtained from N-(β-cyanoethyl) -pyrrolidone [see, e.g., W. Reppe et al., Justus Liebigs Ann. Chem., 596, (1955), p.211]. It is also possible to prepare N-(ω-aminoalkyl)lactones from the corresponding lactones and α,ω-diaminoalkanes (German Patent No. C 730,182). The known processes for the preparation of bicyclic amidines have the disadvantage that they include at least two synthesis steps with working up of the intermediates.

It is known that bicyclic amidines are highly suitable as catalysts for the preparation of polyurethanes (French Patent No. 1,542,058). A considerable disadvantage of this use, however, is that bicyclic amidines are not firmly bonded within the polyurethane formed and therefore, over time, diffuse out of or are extracted from the polyurethane. In each case there is unnecessary pollution of the environment.

BROAD DESCRIPTION OF THE INVENTION

The main object of the invention is to provide an improved and simplified process for the preparation of bicyclic amidines and, from this class of compounds, to provide new compounds which, when used as catalyst for the preparation of polyurethanes, are bonded so firmly to the polymer that they no longer have any notable tendency towards migration. Other objects and advantages of the invention are set out herein or obvious to one skilled in the art.

The objects and advantages of the invention are achieved by the preparation process of the invention, the novel compounds of the invention and the process of using the novel invention compounds.

The invention preparation process involves preparing bicyclic amidines of the general formula:

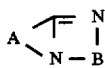

wherein A and B are defined below, in a one-pot process, without isolation or purification of intermediates, from the corresponding lactones of the general formula:

wherein A is defined below, and amines of the general formula:

wherein B is defined below.

The group A in the lactone (II) and in the amidine (I) is in each case a 3-, 4- or 5-membered carbon chain of the formula $-CR^1R^2-CR^3R^4-CR^5R^6-$, $-CR^1R^2-CR^3R^4-CR^5R^6-CR^7R^8-$ or $-CR^1R^2-CR^3R^4-CR^5R^6-CR^7R^8-CR^9R^{10}-$, where $R^1$ and $R^2$ are in each case attached to the carbon atom which is adjacent to the heteroatom.

The group B in the amine (III) and in the amidine (I) is in each case a 2-, 3- or 4-membered carbon chain of the formula $-CR^{11}R^{12}-CR^{13}R^{14}-$, $-CR^{11}R^{12}-CR^{15}R^{16}-CR^{13}R^{14}-$ or $-CR^{11}R^{12}-CR^{15}R^{16}-CR^{17}R^{18}-CR^{13}R^{14}-$.

The general formula I, therefore, encompasses bicyclic amidines having 5-, 6- or 7-membered rings; the two rings can have identical or different numbers of members. Correspondingly, the general formula II encompasses lactones having from 5 to 7 ring members, in other words, γ-, δ- and ε-lactones.

The substituents $R^1$, $R^2$, and $R^{11}$ to $R^{14}$ of the carbon chains A and B are, in each case independently of one another, hydrogen, $C_1-C_4$-alkyl or aryl or $C_1-C_4$-alkyl groups which are in turn substituted with hydroxyl, amino, $C_1-C_4$-alkylamino or mercapto. The substituents $R^3$ to $R^{10}$ and $R^{15}$ to $R^{18}$ can be either the groups mentioned for $R^1$, $R^2$ and $R^{11}$ to $R^{14}$ or else hydroxyl, amino, $C_1-C_4$-alkylamino or mercapto groups.

$C_1-C_4$-alkyl here refers to all primary, secondary and tertiary, unbranched or branched alkyl groups having up to 4 carbon atoms, for example, methyl, ethyl, propyl, butyl, isopropyl, isobutyl, sec-butyl, and tert-butyl. Aryl refers in particular to phenyl or to alkyl-substituted phenyl, such as, o-, m- or p-tolyl or the various isomeric xylyl groups. Examples of suitable lactones are γ-butyrolactone, γ- and δ-valerolactone, ε-caprolactone or substituted lactones such as pantolactone (2-hydroxy-3,3-dimethyl-γ-butyrolactone).

Functional groups as substituents, that is, hydroxyl, amino, alkylamino or mercapto, are preferably located on the groups B of the amine component (III).

Amines (III) which are suitable are therefore not only primary diamines but also compounds having additional primary or secondary amino groups. Examples of suitable amines are 1,2-diaminoethane, 1,2-diaminopropane, 1,3-diaminopropane, 1,2,3-triaminopropane, 1,1,1-tris (aminomethyl)ethane or tetrakis (aminomethyl)-methane. If amines having non-equivalent amino groups are employed, then under some circumstances mixtures of products can be formed—as in the case, for example, with 1,2-diaminopropane or 1,2,3-triaminopropane.

When reacting the lactone (II) with the amine (III) it is advantageous to use a molar ratio of at least 1 mol of amine to 1 mol of lactone (i.e., 1 to 30 mols per mol). Preferably, from 2 to 20 mols of amine are employed per mole of lactone. The excess of amine can be recovered when working up the reaction mixture.

The reaction is advantageously carried out at a temperature of at least 150° C. The reaction temperature is preferably between 200° and 300° C. The addition of an inert solvent, such as, toluene or xylene, while possible, is not necessary. The reaction is preferably carried out without solvent. In order to attain the reaction temperature it is generally necessary to maintain the reaction mixture under elevated pressure, since the boiling points of many starting materials at atmospheric pressure are lower than the reaction temperature. In order to achieve this, customary autoclaves can be employed. In order to accelerate the reaction it is preferable to add an acidic catalyst. Suitable catalysts are Brønsted acids, such as, hydrochloric acid, sulfuric acid, phosphoric acid or ammonium chloride, or alternatively acidic aluminium silicates or acidic metal oxides, such as, tin (IV) oxide or antimony (III) oxide.

In accordance with the invention, the reaction mixture is distilled directly without isolating an intermediate. For practical reasons, this is typically carried out by transferring the reaction mixture from the autoclave to a distillation apparatus. If appropriately equipped apparatus suitable both for superatmospheric pressure and reduced pressure is available, the reaction of the lactone with the amine and the distillation can be carried out in one and the same apparatus. In the distillation, the initial fraction passing over is the water formed during cyclization and the excess amine, followed by the amidine. Depending on the boiling point of the product, the distillation is carried out at an appropriately reduced pressure.

Using the process according to the invention, the known bicyclic amidines mentioned in the background section, such as, DBN and DBU, but also, in particular, novel compounds from this class of substances, having previously unobtained properties, can be prepared.

It has been found that those bicyclic amidines (I) in which at least one of the substituents $R^1$ to $R^{18}$ is and/or carries a primary or secondary amino group, a hydroxyl group and/or a mercapto group can be used as catalyst for the preparation of polyurethanes and are bonded so firmly within the polymer that no migration can be detected either during use or in the course of the customary extraction tests. It is presumed that, during the preparation of the polyurethane, these additional functional groups react with the isocyanate groups of the isocyanate component of the polyurethane and form covalent bonds.

The additional functional groups can of course also be used for other organic reactions with polymeric or nonpolymeric isocyanates, epoxides, carboxylic acids, carboxylic acid derivatives or other compounds.

The additional functional groups are preferably amino groups or aminoalkyl groups, such as, aminomethyl groups. They are preferably located on the chain which in the general formula is designated "B", in other words in the positions of substituents $R^{11}$ to $R^{18}$.

The compounds which are particularly preferred are 3-amino-2,3,4,6,7,8-hexahydropyrrolo[1,2-a]pyrimidine:

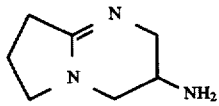

3-(aminomethyl)-2,5,6,7-tetrahydro-3H-pyrrolo[1,2-a]imidazole:

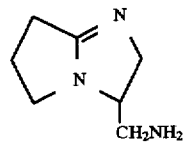

both individually and as a mixture, and 3-(aminomethyl)-3-methyl-2,3,4,6,7,8-hexahydropyrrolo [1,2-a]pyrimidine:

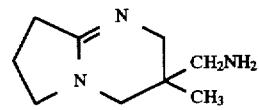

DETAILED DESCRIPTION OF THE INVENTION

The examples which follow will illustrate the implementation of the process according to the invention and the properties and uses of the compounds according to the invention.

EXAMPLE 1

Preparation of 2,5,6,7-tetrahydro-3H-pyrrolo[1,2-a] imidazole (1,4-diazabicyclo[3.3.0]oct-4-ene)

A mixture of 129 g (1.5 mol) of γ-butyrolactone, 8 g (0.15 mol) of ammonium chloride and 360 g (6 mol) of 1,2-diaminoethane was heated at 250° C. in an autoclave. After 2.5 h, the mixture was cooled and the excess diaminoethane and the water formed were removed by distillation. The residue was distilled at 200° C./200 mbar. By heating the distillate in vacuo, the residual water was removed. The yield was 125 g (76%) of colorless oil which gradually solidifies to form a wax-like mass.

EXAMPLE 2

Preparation of 3-amino-2,3,4,6,7,8-hexahydropyrrolo-[1,2-a]-pyrimidine and 3-(aminomethyl)-2,5,6,7-tetrahydro-3H-pyrrolo-[1,2-a]imidazole 21.52 g (0.25 mol) of γ-butyrolactone, 1.34 g (25 mmol) of ammonium chloride and 83.43 g (0.94 mol) of 1,2,3-triaminopropane were reacted analogously to Example 1. The residue which remained after distillative removal of the excess amine and of the water was distilled at 170° to 200° C. (bath temperature)/0.1 mbar. The yield was 22.2 g (64%) of yellowish oil. The boiling point was 95°–97° C./2 mbar.

According to GC, the product consisted of about 90 percent of the isomer having the pyrrolo[1,2-a]pyrimidine structure and about 10 percent of the isomer having the pyrrolo[1,2-a]imidazole structure:

3-Amino-2,3,4,6,7,8-hexahydropyrrolo[1,2-a]pyrimidine
$^1$H-NMR (CDCl$_3$, 400 MHz) δ: 1.96 (quint, 2H, H-7);
2.45 (t, 2H, H-8);
2.7–2.8 (m, 1H, H-4$_a$);
3.05 (t, 1H, H-2$_a$);
3.1–3.2 (m, 1H, H-3);
3.3 (t, 2H, H-6);
3.35 (t, 1H, H-4$_b$);
3.45–3.5 (m, 1H, H-2$_b$).
$^{13}$C-NMR (100 MHz) δ: 160.5 (s, C-8a);
52.88 (t, C-2);
51.4 (t, C-6);
50.9 (t, C-4);

43.0 (t, C-3);
30.9 (t, C-8);
20.0 (t, C-7).

3-(Aminomethyl)-2,5,6,7-tetrahydro-3H-pyrrolo[1,2-a]-imidazole $^1$H-NMR (CDCl$_3$, 400 MHz) δ: 2.28–2.32 (m, 2H, H-6);
2.32–2.35 (m, 2H, H-7);
2.75 (m, 1H, CH$_a$NH$_2$);
2.85 (m, 2H, H-5);
3.3 (m, 1H, CH$_b$NH$_2$);
3.4 (m, 1H, H-3);
3.8 (dd, 1H, H-2$_a$);
4.15 (dd, 1H, H-2$_b$).

$^{13}$C-NMR (CDCl$_3$, 100 MHz) δ: 175.8 (s, C-7a);
64.5 (t, C-2);
64.3 (d, C-3);
45.8 (t, CH$_2$NH$_2$);
44.3 (t, C-5);
25.4 (t, C-7);
22.6 (t, C-6).

EXAMPLE 3

Preparation of 3-(aminomethyl)-3-methyl-2,3,4,6,7,8-hexahydropyrrolo[1,2-a]pyrimidine A mixture of 21.03 g (0.24 mol) of γ-butyrolactone and 1.31 g (24 mmol) of ammonium chloride in 114.5 g (0.98 mol) of 1,1,1-tris(aminomethyl)ethane was heated at 250° C. in an autoclave. After 1.5 h, the mixture was cooled and the excess amine and the water formed were removed by distillation. The residue was distilled at 200°–240° C./18 mbar. The yield was 22.0 g (54%) of yellowish oil. The boiling point was 117°–120° C./1 mbar. Other data concerning the product was:

$^1$H-NMR (CDCl$_3$, 400 MHz) δ: 0.91 (s, 3H, CH$_3$);
1.95 (quint, 2H, H-7);
2.45 (t, 2H, H-8);
2.53 (dd, 2H, CH$_2$NH$_2$);
2.84 (dd, 1H, H-4$_a$);
3.0 (m, 2H, H-2$_a$, H-4$_b$);
3.13 (dd, 1H, H-2$_b$);
3.28 (dt, 2H, H-6).

$^{13}$C-NMR (CDCl$_3$, 100 MHz) δ: 160.1 (s, C-8a);
53.5 (t, C-2);
51.5 (t, C-6);
51.3 (t, C-4);
48.5 (t, CH$_2$NH$_2$);
32.0 (s, C-3);
30.9 (t, C-8);
20.9 (q, CH$_3$);
19.9 (t, C-7).

EXAMPLE 4

Preparation of 2,5,6,7-tetrahydro-3H-pyrrolo[1,2-a]-imidazole

A mixture of 86 g (1 mol) of γ-butyrolactone and 2 ml of 98 percent strength sulfuric acid in 240 g (4 mol) of 1,2-diaminoethane was heated at 250° C. in an autoclave. After 4.5 h, the reaction mixture was cooled and worked up as described in Example 1. The yield was 90 g (82%). For properties of the product, see Example 1.

EXAMPLE 5

Preparation of 2,3,4,6,7,8-hexahydropyrrolo[1,2-a]pyrimidine (1,5-diazabicyclo[4.3.0]non-5-ene, DBN)

A mixture of 43 g (0.5 mol) of γ-butyrolactone and 2.68 g (25 mmol) of ammonium chloride in 148 g (2 mol) of 1,3-diaminopropane was heated at 250° C. in an autoclave. After 4.5 h, the mixture was cooled and the excess amine and the water formed were removed by distillation up to 250 mbar. The residue was distilled in vacuo. The yield was 47 g (75%) of colorless liquid. The boiling point was 98° C./12 mbar.

EXAMPLE 6

Preparation of 2,3,4,6,7,8,9,10-octahydropyrimido[1,2-a]azepine (1,8-diazabicyclo[5.4.0]undec-7-ene, DBU)

The procedure described in Example 5 was followed with the difference that, instead of γ-butyrolactone, 57 g (0.5 mol) of ε-caprolactone was employed. The yield was 16 g (21%) of colorless liquid. The boiling point was 115° C./8 mbar.

EXAMPLES 7 to 9

Preparation of polyurethanes using bicyclic amidines as catalyst

General Procedure

At room temperature 50 g of an aromatic polyisocyanate based on diphenylmethane diisocyanate (about 32 percent of NCO) was added, while stirring with a glass rod, to a solution of 0.5 g of the amidine in 55 g of a trifunctional, hydroxyl-containing branched polyether (Desmophen® 550 U, about 11.5 percent of OH). A film about 200 μm thick was cast from each mixture. After curing had been carried out, the migration capacity of the amidine was determined by extraction testing. For this purpose, 10 g of each of the films thus obtained, cut into small pieces, were stored in 40 ml of methanol at room temperature. After various intervals, the amidine content in samples of the methanol was determined by GC.

EXAMPLE 7 (COMPARISON EXAMPLE)

The amidine employed was 2,3,4,6,7,8-hexahydropyrrolo-[1,2-a]pyrimidine (DBN). The gel time was 3 mins., 15 s. The amidine content in the extraction test was:

after 1 h about 0.012% after 1 day about 0.06% after 14 days about 0.1%

After 14 days, therefore, the majority of the total amount of amidine present had been extracted.

EXAMPLE 8

The amidine employed was a mixture of about 90 percent of 3-amino-2,3,4,6,7,8-hexahydropyrrolo[1,2-a]pyrimidine and about 10 percent of 3-(aminomethyl)-2,5,6,7-tetrahydro-3H-pyrrolo[1,2-a]imidazole (prepared according to Example 2). The gel time was 3 mins, 30 s. The amidine content was:

after 1 h<10 ppm after 1 day<10 ppm after 14 days<10 ppm

EXAMPLE 9

The amidine employed was 3-(aminomethyl)-3-methyl-2,3,4,6,7,8-hexahydropyrrolo[1,2-a]pyrimidine (prepared according to Example 3). The gel time was 3 mins. The amidine content was:

after 1 h<10 ppm after 1 day<10 ppm after 14 days<10 ppm

In the case of the amidines, according to the invention, the extracted quantity, even after 14 days, was still below the detection limit.

EXAMPLE 10 to 12

General procedure

At room temperature, 40 g of an aliphatic triisocyanate (about 23 percent of NCO) was added, while stirring with a glass rod, to a solution of 0.44 g of the amidine and 30 mg of dibutyl tin dilaurate in a mixture comprising in each case 24 g of a trifunctional, hydroxyl-containing branched polyether (Desmophen® 550 U, about 11.5 percent of OH and Desmophen® 1915 U, about 1.1 percent of OH). A film about 200 μm thick was cast from the mixture and the procedure of Examples 7 to 9 was then followed.

EXAMPLE 10 (COMPARISON EXAMPLE)

The amidine employed was 2,3,4,6,7,8-hexahydropyrrolo[1,2-a]pyrimidine (DBN). The gel time was 70 s. The amidine content in the extraction test was:

after 1 day<10 ppm
after 14 days<10 ppm
after 2 months 0.03%

EXAMPLE 11

The amidine employed was a mixture of about 90 percent of 3-amino-2,3,4,6,7,8-hexahydropyrrolo[1,2-a]pyrimidine and about 10 percent of 3-(aminomethyl)-2,5,6,7-tetrahydro-3H-pyrrolo[1,2-a]-imidazole (prepared according to Example 2). The gel time was 75 s. The amidine content was:

after 1 h<10 ppm
after 14 days<10 ppm
after 2 months<10 ppm

EXAMPLE 12

The amidine employed was 3-(aminomethyl)-3-methyl-2,3,4,6,7,8-hexahydropyrrolo[1,2-a]pyrimidine (prepared according to Example 3). The gel time was 65 s. The amidine content was:

after 1 h<10 ppm
after 1 day<10 ppm
after 2 months<10 ppm

Examples 10 to 12 also exhibit, after a long period of testing (2 months), a considerable reduction in the tendency towards migration.

What is claimed is:

1. A process for the preparation of a bicyclic amidine of the formula:

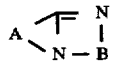

wherein A is selected from the group consisting of —$CR^1R^2$—$CR^3R^4$—$CR^5R^6$—, —$CR^1R^2$—$CR^3R^4$—$CR^5R^6$—$CR^7R^8$— and —$CR^1R^2$—$CR^3R^4$—$CR^5R^6$—$CR^7R^8$—$CR^9R^{10}$—, wherein the substituents in A are in each case numbered starting from the nitrogen atom, and B is selected from the group consisting of —$CR^{11}R^{12}$—$CR^{13}R^{14}$—, —$CR^{11}R^{12}$—$CR^{15}R^{16}$—$CR^{13}R^{14}$—, and —$CR^{11}R^{12}$—$CR^{15}R^{16}$—$CR^{17}R^{18}$—$CR^{13}R^{14}$—, and $R^1$, $R^2$ and $R^{11}$ to $R^{14}$ are, in each case independently of one another, hydrogen, $C_1$–$C_4$-alkyl, aryl, or are $C_1$–$C_4$-alkyl which is substituted with hydroxyl, primary amino, mono-$C_1$–$C_4$-alkylamino or mercapto, and $R^3$ to $R^{10}$ and $R^{15}$ to $R^{18}$ are, in each case independently of one another, hydrogen, $C_1$–$C_4$-alkyl, aryl, hydroxyl, primary amino, mono-$C_1$–$C_4$-alkylamino or mercapto, or are $C_1$–$C_4$-alkyl which is substituted with hydroxyl, primary amino, mono-$C_1$–$C_4$-alkylamino or mercapto, wherein the substituents $R^{11}$ and $R^{12}$ in B are in each case numbered starting from the nitrogen atom having a double bond, comprising heating a lactone of the formula:

wherein A is as defined above, to at least 150° C. together with an at least equimolar quantity of an amine of the formula:

wherein B is as defined above, and subjecting the resultant reaction mixture, without isolating an intermediate, to a fractional distillation to provide the bicyclic amidine of formula I.

2. The process according to claim 1 wherein the reaction of the lactone (II) with the amine (III) is carried out in the presence of an acidic catalyst.

3. The process according to claim 2 wherein the amine (III) is employed in a quantity of from 2 to 20 mols per mole of the lactone (II).

4. The process according to claim 3 wherein the lactone (II) employed is a compound selected from the group consisting of γ-butyrolactone, γ-valerolactone, δ-valerolactone, ε-caprolactone and pantolactone.

5. The process according to claim 4 wherein the amine (III) employed is a compound selected from the group consisting of 1,2-diaminoethane, 1,2-diaminopropane, 1,3-diaminopropane, 1,2,3-triaminopropane, 1,1,1-tris(aminomethyl)ethane and tetrakis-(aminomethyl)methane.

6. The process according to claim 1 wherein the amine (III) is employed in a quantity of from 2 to 20 mols per mole of the lactone (II).

7. The process according to claim 1 wherein the lactone (II) employed is a compound selected from the group consisting of γ-butyrolactone, γ-valerolactone, δ-valerolactone, ε-caprolactone and pantolactone.

8. The process according to claim 1 wherein the amine (III) employed is a compound selected from the group consisting of 1,2-diaminoethane, 1,2-diaminopropane, 1,3-diaminopropane, 1,2,3-triaminopropane, 1,1,1-tris(aminoethyl)ethane and tetrakis-(aminomethyl)methane.

* * * * *